(12) United States Patent
Chiang

(10) Patent No.: US 6,818,415 B2
(45) Date of Patent: Nov. 16, 2004

(54) SODIUM ACTIVATION OF AMYLASE

(75) Inventor: Vincent Chiang, Sunnyvale, CA (US)

(73) Assignee: Abaxis, Inc., Union City, CA (US)

(*) Notice: Subject to any disclaimer, the term of this patent is extended or adjusted under 35 U.S.C. 154(b) by 46 days.

(21) Appl. No.: 09/887,628

(22) Filed: Jun. 22, 2001

(65) Prior Publication Data

US 2003/0022264 A1 Jan. 30, 2003

(51) Int. Cl.$^7$ ................................................. C12Q 1/40
(52) U.S. Cl. ........................................................ 435/22
(58) Field of Search .......................................... 435/22

(56) References Cited

U.S. PATENT DOCUMENTS

| 4,657,854 A | 4/1987 | Wegfahrt, Jr. ................. 435/14 |
| 5,229,270 A | 7/1993 | Ono et al. ..................... 435/22 |

FOREIGN PATENT DOCUMENTS

| JP | 01-181799 | * 7/1989 |
| JP | 11-266898 | * 10/1999 |
| WO | 99/50444 | * 10/1999 |

OTHER PUBLICATIONS

Lifshitz, Ruth and Levitzki, Alexander, "*Identity and Properties of the Chloride Effector Binding Site in Hog Pancreatic α–Amylase,*" Biochemistry, vol. 15, No. 9, 1976, pp. 1987–1999.

Levitzki, Alexander and Steer, Michael L., "*The Allosteric Activation of Mammalian α–Amylase by Chloride*" Eur. J. Biochem, 41, 1974, pp. 171–180.

* cited by examiner

*Primary Examiner*—Sandra E. Saucier
(74) *Attorney, Agent, or Firm*—Gray, Cary, Ware & Freidenrich LLP

(57) ABSTRACT

Chloride ion and sodium ion determination methods, compositions, and assays are provided which are based on the use of sodium ion as an activator for α-amylase. Chloride ion and sodium ion determination are performed by colorimetry, using measurements of α-amylase activity to indirectly measure the desired ion concentrations. One preferred composition for chloride ion determination comprises α-amylase that is substantially calcium free, sodium ion in higher concentration than the α-amylase, and an α-amylase activity detecting substrate. In the methods, α-amylase is deactivated by a calcium-binding compound, thereby preventing calcium from bonding with the α-amylase. Next, chloride ion and sodium ion stoichiometrically bond with deactivated α-amylase, thereby activating the α-amylase. Chloride ion determination methods are based on using test sample chloride as the limiting factor in α-amylase activation and sodium ion determination methods are based on using test sample sodium as the limiting factor in α-amylase activation.

20 Claims, 4 Drawing Sheets

SODIUM ACTIVATION OF AMYLASE

BACKGROUND OF THE INVENTION

1. The Field of the Invention

The present invention relates to methods, compositions, and assays for the determination of chemical components in biological samples. More particularly, the present invention relates to calorimetric assays based on the sodium activation of amylase.

2. The Relevant Technology

Chloride ion is the major extracellular negative ion in the human body. Its main function is to maintain electrical neutrality by acting as a counter-ion to sodium. Accordingly, chloride ion levels often accompany sodium losses and excesses. Chloride ion also helps regulate acid-base balances by entering cells in response to rising carbon dioxide levels. As carbon dioxide increases, bicarbonate moves from the intracellular space to the extracellular space. In response, chloride tends to enter the cells.

Therefore, there are various circumstances where it is important to analyze serum and other bodily fluids to determine the amount of chloride ion. For example, hyperchloremia (high serum chloride) may indicate chronic hyperventilation, Cushing's syndrome, dehydration, eclampsia, excess infusion of normal saline, kidney dysfunction, metabolic acidosis, or renal tubular acidosis. Hypochloremia (low serum chloride) may indicate Addison's disease, burns, chronic respiratory acidosis (chronic hypoventilation), congestive heart failure, excessive sweating, gastric suction, over hydration, salt-losing nephritis, syndrome of inappropriate ADH secretion, or vomiting.

In response to this need, there have been developed various methods and devices to analyze bodily fluids and determine the amount of chloride ion in a sample. One early method was a calorimetric test of free chlorine. It detected the presence of the chloride ion by using a soluble silver salt and tolidine. However, this method lacked the precision required by most applications.

The need for more precise chloride ion measurements has led to the development of more accurate tests through a variety of methods. Most current methods for the determination of chloride ion are based on either electric or chemical methods. Electric methods include coulometric titration and the ion selective electrode method. The coulometric titration method is considered the most reliable method, if not the quickest. It can be performed with either manual or semi-automatic methods, but is difficult to perform in an automatic analytical system. The ion selective electrode method can have specificity problems and is prone to interference from proteins and surfactants.

The principal chemical method is colorimetry, wherein the concentration of the chloride ion is measured according to changes in color density. The colorimetry method is considered the most effective test for simple applications because it is less complicated than coulometric or ion selective electrode methods. The most common chloride determination colorimetry methods react mercuric thiocyanate and chloride ion to produce thiocyanate ion, which then forms a complex with ferric ion. The result is a characteristic red orange color, which deepens as the concentration of the chloride ion becomes higher, thus enabling colorimetry. Nevertheless, this method has drawbacks because both mercuric ions and the thiocyanate ions are harmful to the environment. As a result, each use of the reagents creates additional waste that requires costly care and treatment. Therefore, there is a need for calorimetric methods to determine chloride ion concentration that avoid the mercuric and thiocyanate ions.

U.S. Pat. No. 5,229,270 to Ono et al. (hereinafter "Ono") discloses an environmentally safe quantitative assay and reagent for the determination of chloride ion in bodily fluids. Ono uses a reagent which contains deactivated $\alpha$-amylase, a compound capable of chelating calcium ion, a calcium chelate ion, a calcium chelate compound, and an $\alpha$-amylase measuring substance. The method comprises the steps of: (a) contacting a bodily fluid sample suspected of containing chloride ions with a reagent which comprises a compound capable of forming a chelate with a calcium ion, deactivated $\alpha$-amylase, a calcium chelate compound, and an $\alpha$-amylase activity-measuring substance; (b) determining the quantity of $\alpha$-amylase activity formed due to the presence of chloride ions in the bodily fluid sample, which is directly proportional to the amount of chloride ions present in the bodily fluid sample; and (c) determining the quantity of the chloride ions from the quantity of the $\alpha$-amylase activity by referring to a calibration curve. This method is capable of automation and has high ion specificity.

It has previously been shown that $\alpha$-amylase contains one chloride ion binding site per molecule. One early approach at describing the chloride ion effects on $\alpha$-amylase is described in Lifshitz, Ruth, Levitski, Alexander, *Identity and Properties of the Chloride Effector Binding Site in Hog Pancreatic $\alpha$-Amylase*, Biochemistry, Vol. 15, No. 9, 1976. (hereinafter, "Lifshitz"). Lifshitz is specifically directed to determine the chloride ion binding site in $\alpha$-amylase. In reaching their conclusions, Lifshitz discusses various compounds and their effects upon the chloride ion binding site. For example, Lifshitz teaches that calcium-free $\alpha$-amylase is unable to bind chloride ion. Similarly, Lifshitz tested sodium fluoride (fluoride ion) and sodium acetate (acetate ion) to determine their effect upon the chloride ion affinity of deactivated $\alpha$-amylase. Lifshitz determined that neither fluoride ion nor sodium acetate had any appreciable effect upon the chloride ion affinity of deactivated $\alpha$-amylase. Lifshitz at 1990.

Notwithstanding the prior methods for assaying chloride ions using calcium-activated $\alpha$-amylase, there remains a continuing need for alternative systems for assaying chloride.

BRIEF SUMMARY OF THE INVENTION

It is an object of the present invention to provide alternative methods, compositions, and assays to determine the quantity of chloride ion in biological samples.

It is another object of the present invention to provide alternative methods, compositions, and assays to determine the quantity of sodium ion in biological samples.

It is a further object of the invention to provide a chloride assay that is environmentally safe.

It is a yet a further object of the invention to provide a chloride assay that is simple to perform yet accurate.

In accordance with the present invention, there is provided a method for the determination of chloride ion in biological fluids. To perform clinical assays incorporating the discoveries of the present invention, one method for determining the concentration of chloride ions in samples comprises first preparing an enzyme reagent which includes $\alpha$-amylase that is substantially calcium-free and an $\alpha$-amylase activity detecting substrate. Next, the enzyme reagent, sodium ion, and a sample containing chloride ion to be assayed are combined, wherein the sodium ion is present in a higher concentration than the chloride ion. The quantity of α-amylase activated due to the presence of sodium ions and chloride ions in the sample is then assayed. Finally, the quantity of the chloride ions is determined by reference to the assay of α-amylase.

A composition for use in determining the concentration of chloride ions in bodily fluid samples comprises α-amylase that is substantially calcium-free, an α-amylase activity detecting substrate, and sodium ion, wherein the concentration of sodium ion is higher than that of the chloride ion to be assayed.

Yet another aspect of the invention comprises a method for determining the concentration of sodium ions in bodily fluid samples. The method comprises first preparing an enzyme reagent which includes α-amylase that is substantially calcium-free and an α-amylase activity detecting substrate. Next, the enzyme reagent, chloride ion, and a sample containing sodium ion to be assayed are combined, wherein the chloride ion is present in a higher concentration than the sodium ion. The quantity of α-amylase formed due to the presence of sodium ions and chloride ions in the sample is then assayed. Finally, the quantity of the sodium ions is determined by reference to the assay of α-amylase.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
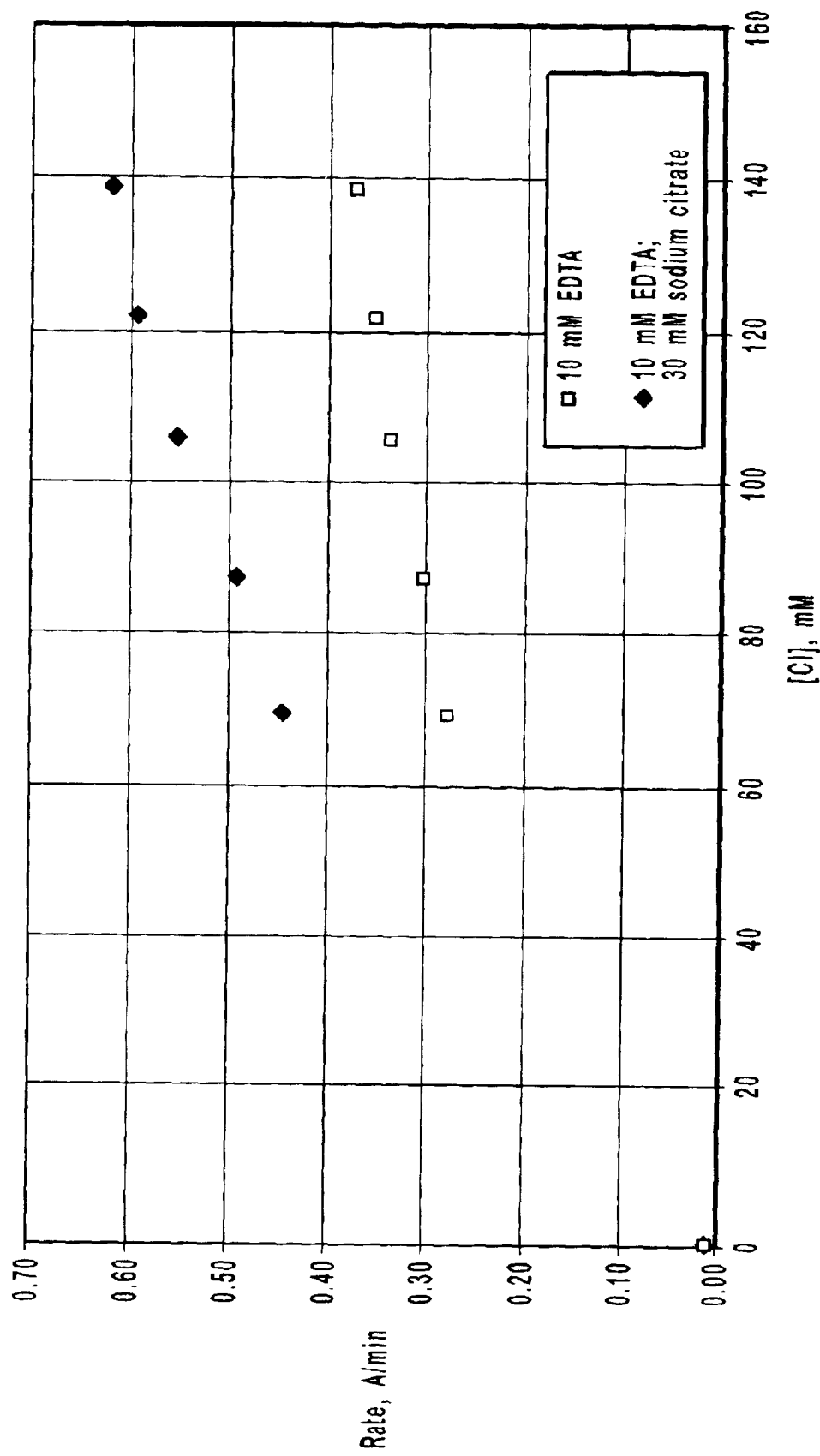
FIG. 1 is a graph showing comparative assays that demonstrate the effect of sodium citrate on chloride ion determination according to the invention.

The present invention relates to methods, systems, and compositions based on the discovery that sodium ion functions as an activator for α-amylase. More particularly, the present invention relates to calorimetric assays based on the discovery that sodium activates amylase even in the absence of calcium. Preferred aspects of the invention are directed to the determination of chloride ion and sodium ion in biological samples. In particular, assays where calcium activation of amylase is undesirable can utilize the sodium activation of amylase as a substitute.

With regards to the determination of chloride ion in a bodily fluid sample, a calcium binding compound is first used to remove all calcium from the bodily fluid sample so as to ensure the enzyme is not activated by the presence of calcium in the system. The addition of chloride ion and excess sodium ion then enables sodium ion to bind with deactivated α-amylase thus activating the α-amylase at a level proportional to the amount of chloride ion. Although the present invention is not limited to any particular theory, it is believed that the sodium ion activates amylase by a mechanism similar to that of the calcium ion.

The novel methods and systems according to the invention are preferably performed by colorimetry, using measurements of α-amylase activity to indirectly measure the chloride ion concentration. The methods and systems involve one or more measurements of a detectable product of α-amylase activity at a specified time or times after the enzymatic reaction is initiated. From correlations with known data, the system assays for total chloride ion. Alternatively, the system can be used to assay for sodium ion concentration using excess chloride ion in a sample with an unknown sodium ion concentration.

The invention can be used with a variety of samples. Of particular interest are biological samples known to contain chloride ion in measurable quantities. For example, serum, plasma, and urine are known to have quantifiable amounts of chloride that can be used as a sign of metabolic function of electrolytes. Of course, the present invention can be used in other applications where chloride ion determination is desired. Therefore, the invention also encompasses a method for the determination of chloride ion concentration of non-bodily fluids as well.

Referring now to the reagents according to the present invention, one method according to the present invention comprises first preparing an enzyme reagent which includes α-amylase that is substantially calcium-free and an α-amylase activity detecting substrate. Next, the enzyme reagent, sodium ion, and a sample containing chloride ion to be assayed are combined, wherein the sodium ion is present in a higher concentration than the chloride ion. The quantity of α-amylase formed due to the presence of sodium ions and chloride ions in the sample is then assayed. Finally, the quantity of the chloride ions is determined by reference to the assay of α-amylase.

The sodium ion compound is preferably included either by addition to the enzyme reagent or by later addition to the combined solution.

As indicated, the enzyme used according to the present invention is α-amylase. Alpha-amylases are enzymes that catalyze the hydrolysis of complex carbohydrates into maltose and residual glucose. It is well known that α-amylase is active when coupled with the calcium ion and it has been believed that removal of calcium ion results in deactivated α-amylase (hereinafter "apo-AMY"). However, it has been surprisingly discovered that sodium ion also functions as an activator of α-amylase, even in the absence of calcium ions.

A preferred class of substances that removes calcium from α-amylase are chelating compounds, such as ethylenediaminetetraacetic acid (EDTA), that are capable of forming a chelate with calcium. Calcium-chelating compounds form a highly stable complex between a calcium ion and more than one organic group to form a ring, thus depriving intermixed chemicals of calcium. In sufficiently high concentrations, chelating compounds substantially deactivate the α-amylase by chelating substantially all of the calcium. However, chelating compounds do not permanently bind the calcium ion. When apo-AMY in the presence of calcium-EDTA, for example, is reacted with high concentration chloride ion, the apo-AMY is again coupled with the calcium ion to form active-AMY. See A. Levitzki and M. L. Steer, *The Allosteric Activation of Mammalian α-Amylase by Chloride*, Eur. J. Biochem. 41, p. 171 (1974). In addition to EDTA, other preferred calcium-chelating compounds include trans-1,2-cyclohexanediamine-N,N,N',N'-tetraacetic acid, glycol ether diamine tetraacetic acid, iminotetraacetic acid, and diaminopropanetetraacetic acid Because of the reversibility of this calcium removal, one has to guard against activation of the amylase by calcium because that would interfere with the assay of this invention. One approach is to maintain a sufficiently high calcium-chelating compound concentration to ensure that all substantially all calcium is bound, thus minimizing the reverse reaction.

A calcium-chelate compound is in principle a chelate of the above calcium-chelating compound with calcium ion. Examples of calcium-chelate compounds include calcium ethylenediaminetetraacetate (Ca-EDTA), calcium trans-1,2-cyclohexanediamine-N,N,N',N'-tetraacetate, calcium iminotetraacetate, and calcium diaminopropanetetraacetate. As EDTA is preferable, the use of Ca-EDTA is also preferable.

Another class of substances that removes calcium from test samples is compounds that form a covalent bond with calcium. This allows the permanent removal of calcium from the test sample, with no risk of a reverse reaction releasing calcium and destroying the accuracy of the assay.

Because α-amylase functions in biological systems to split complex carbohydrates and therefore has biological significance apart from the objects of the present invention, various detecting means have been developed and are known in the art. Alpha-amylase detecting means that are suitable for use in the present invention include substrates that are hydrolyzed by α-amylase and release substances which are detectable by calorimetric methods. In the preferred case, active-AMY hydrolyzes 2-chloro-4-nitrophenyl-α-D-maltotrioside (CNPG3) to form 2-chloro-4-nitrophenol, 2-chloro-4-nitrophenyl-α-D-maltoside (CNPG2), maltotriose and glucose. The reaction is depicted in the following equation:

Equation 1

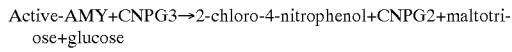

Active-AMY+CNPG3→2-chloro-4-nitrophenol+CNPG2+maltotriose+glucose

The rate of formation of the 2-chloro-4-nitrophenol can be measured in a spectrophotometer at 405 nm to give a direct measurement of active-AMY in the sample.

Alternatively, the α-amylase detecting substrate may comprise a substrate 18 composition that utilizes a coupling enzyme. For example, preferred compositions include a substance comprised of 4-nitrophenyl-α-D-maltopentaoside as substrate and α-glucosidase as coupled enzyme, a substance comprised of 2-chloro-4-nitrophenyl-β-D-maltopentaoside as substrate and α-glucosidase and β-glucosidase as coupled enzyme, a substance comprised of 4-nitrophenyl-β-D-maltoheptaoside as substrate and α-glucosidase as coupled enzyme, and a substance comprised of 2-chloro-4-nitrophenyl-b-D-maltoheptaoside as substrate and α-glucosidase and β-glucosidase as coupled enzyme. In these embodiments, the α- and β-glucosidases are coupling enzymes that hydrolyze an intermediate product, such as 4-nitrophenyl-α-D-maltose, 4-nitrophenyl-α-D-maltotriose, 2-chloro-4-nitrophenyl-β-D-maltose or 2-chloro-4-nitrophenyl-β-D-maltotriose, to the final product, i.e. 4-nitrophenol or 2-chloro-4-nitrophenol.

Of course, one skilled in the art will recognize, in light of the disclosure herein, that other currently known or future developed α-amylase detecting substrate or methods can be used in the present invention.

Sodium ion compounds according to the invention include any of a variety of substances that release sodium ion when added to the reagents of the present invention. For example, preferred sodium ion compounds include sodium acetate and sodium citrate.

Because the methods of the present invention involve enzymatic reactions, the pH value must be maintained within suitable ranges. Preferably, the pH is maintained between 7 and 9. Most conventional buffers can be used to maintain the pH in this range. Examples of suitable buffers include triethanolamine (TEA), 3-morpholinopropane sulfonic acid (MOPS), phosphate buffer, tris-HCl, citrate buffer, and tricine.

Other components are also included to maintain the solution at a constant state when a bodily fluid sample is added. Preferred components of the substrate reagent typically include one or more of lithium hydroxide (LiOH), octoxynol (commercially available from Rohm and Haas under the name "Triton X"), trehalose, polyethylene glycol 8000 (PEG 8000), and bovine serum albumin (BSA).

Other preferred components of the enzyme reagent optionally include one or more of 22 LiOH, dextran, trehalose, PEG 8000, and BSA. Of course, one skilled in the art will recognize that a variety of substances can be used to formulate a composition that will maintain a constant state when a bodily fluid sample is added.

Advantageously, as can be readily observed from the reagent components cited above, the reagents of this invention do not contain environmentally hazardous materials. Therefore, the present invention has the advantage of simpler handling and disposal requirements than many prior art chloride ion determination methods and reagents.

Referring now to the methods for chloride ion determination according to the present invention, one preferred method comprises first preparing an enzyme reagent, which includes α-amylase that is substantially calcium free and an α-amylase activity detecting substrate. The α-amylase that is substantially calcium free is provided by use of one of the calcium binding compounds discussed hereinabove. Next, the enzyme reagent, sodium ion, and a sample suspected of containing chloride ion are combined, wherein the sodium ion is present in a higher concentration than the chloride ion. The quantity of activated α-amylase formed due to the presence of chloride ions in the bodily fluid sample is then determined by assay. Finally, the quantity of chloride ions is indirectly determined from the directly measured activity of the α-amylase. The concentration of chloride ion within a range of about 60–140 mM in a sample can be determined with the above method.

In the case of the use of a calcium-chelating compound, the calcium-chelating compound functions not only to initially deactivate the α-amylase, but also to stabilize the apo-AMY. It is difficult to remove all calcium ion from the reagent because the calcium-chelate in the reagent contains calcium. Thus, a small portion of the apo-AMY is supplied with calcium ion and is converted into the active-AMY even in the absence of chloride ion. The result of this unintended reaction is that a blank reagent (blank reaction) in the data obtained, causing inaccuracy of the measurement. The calcium-chelating compound effectively inhibits the reverse reaction of the apo-AMY to active-AMY by preventing the above-mentioned undesirable reaction. Thus, to ensure accuracy, any calcium ion that may be present is minimized by using a sufficient concentration of calcium-chelating compound. Any remaining calcium ion is accounted for by running a blank sample.

The concentration of each component in the assay solution is controlled so that the concentration of chloride ions in the sample is rate-controlling. Preferably, the substrate and other necessary reactants are maintained in excess so that the only limiting factor is the chloride ion concentration. Further, the process ideally limits the rate of loss of the detectable reactant so that rate of loss is not necessarily included. The reactants other than chloride ion are present in concentrations sufficiently high to not significantly limit the rate of the reaction over the period of the analysis. Thus, measurement of the α-amylase or product concentration at a specified time or times after the reaction is initiated is a measure of the rate of loss of α-amylase or of production of the detectable product, and provides data which are correlated to chloride ion concentration.

Thus, according to the invention, a selected volume of a chloride ion standard or biological fluid sample suspected of containing chloride ion is combined with a selected volume of the above reagents and mixed, initiating the reactions. This method can preferably be performed in an automatic analytical system for serum as is common in the art.

The reaction progress can preferably be measured by introducing the mixture to a quartz cuvette, and placing the cuvette in a spectrophotometer. At a specified time or times after the initiation of the reaction, the absorbance at about 405 nm is read and recorded. According to the present invention, measurement of the α-amylase detecting substrates can be performed with spectrophotometers as are currently known in the art. Such spectrophotometers are widely available in chemical and clinical laboratories. Further, this method can preferably be performed in an automatic analytical system for serum as is common in the art. Therfore, the present invention has the advantage that the various apparatuses required to practice the invention are widely available.

Preparation of a calibration curve for use with the present invention may be performed in the following manner. First, the reagent to be used in later tests is mixed with a series of known samples containing incremental concentrations of chloride ion. The sample chloride concentrations are selected to roughly correspond to the expected chloride ranges to be tested. For example, chloride ion concentration in serum typically falls within a range of about 70–130 mM. Next, the activity of the α-amylase is then measured in each sample test by the procedures taught hereinabove. Finally, the α-amylase is then plotted in a calibration curve as α-amylase activity versus chloride ion concentration. The chloride ion concentration can then be determined in a sample by locating the absorbance from the sample on the calibration curve showing the absorbance of the standard(s) as a function of chloride ion concentration.

Alternatively, chloride ion concentration can be calculated by inserting data for the absorbance of the sample, the absorbance of a standard, and the concentration of the sample into an equation, from which the chloride ion concentration can be calculated. One example equation is:

$$Cl \text{ concentration} = K \frac{(\text{absorbance of sample})(\text{concentration of sample})}{(\text{absorbance of standard})} \quad \text{Equation 2}$$

wherein K is a constant dependent upon the components of the assay solution, their concentrations, and the volumes of the sample and assay solution.

Yet another chloride ion calculation method is performed by measuring the absorbance at two or more predetermined times following the initiation of the reaction. The absorbance readings must be corrected for any background absorbencies or the reaction rate of the reagent. The corrected absorbance readings are then plotted versus time, a connecting line is drawn, and the slope of the line is calculated. The slope of the line directly correlates to the reaction rate, and can be compared to known slopes to find a similarly determined rate for a standard of known chloride ion concentration.

The above reagents and methods can be modified, in view of the disclosure herein, for use in the determination of sodium ion. For example, one preferred method comprises first preparing an enzyme reagent, which includes α-amylase that is substantially calcium-free, an α-amylase activity detecting substrate, and chloride ion. Next, the enzyme reagent, a sample suspected of containing sodium ion, and optionally a calcium-binding compound are combined. The calcium binding compound can be used to ensure that no calcium in the sample affects the accuracy of the assay. The quantity of α-amylase activity formed due to chloride ion and sodium ion (and calcium ion) in the bodily fluid sample is then assayed. Finally, the quantity of sodium ions is determined by reference to the assay of α-amylase. Whereas the chloride ion determination reagents and methods are designed so that chloride ion concentration is the limiting factor in the enzymatic reactions, the sodium ion determination reagents and methods are designed so that sodium ion is the limiting factor. Sodium ion determination methods also include the additional step of accounting for any calcium ion that may be present in the sample. If no calcium-binding compound is used, it is preferable to determine the amount of calcium in the sample before performing the above assay.

The following examples are given to illustrate the present invention, and are not intended to limit the scope of the invention.

EXAMPLE 1

A calcium-containing substrate reagent and an enzyme reagent were prepared according to Table 1 and Table 2 respectively below. Assays were conducted with and without the addition of 30 mM sodium citrate to the enzyme reagent. The results are plotted in FIG. 1 with the rate in A/min plotted versus chlorine concentration in mM. It was determined that the addition of sodium citrate in the enzyme reagent resulted in higher reaction rates than without the sodium citrate.

TABLE 1

| SUBSTRATE REAGENT | CENCENTRATION |
|---|---|
| CNPG3 | 5 mM |
| TEA | 80 mM |
| LiOH | 100 mM |
| EDTA | 30 mM |
| Ca Acetate | 7 mM |
| Triton X | 0.19% |
| Trehalose | 2% |
| PEG 8000 | 4% |
| BSA | 2% |

TABLE 2

| ENZYME REAGENT | CONCENTRATION |
|---|---|
| Amylase | 15000 U/L |
| MES | 10 mM |
| LiOH | 30 mM |
| EDTA | 10 mM |
| Dextran | 3% |
| Trehalose | 5% |

TABLE 3

| SUBSTRATE REAGENT | CONCENTRATION |
|---|---|
| CNPG3 | 5 mM |
| TEA | 50 mM |
| LiOH | 40 mM |
| EDTA | 40 mM |
| Sodium citrate | 30 mM, 60 mM |
| Trehalose | 2% |
| PEG 8000 | 4% |
| BSA | 2% |

TABLE 4

| ENZYME REAGENT | CONCENTRATION |
|---|---|
| Amylase | ~15000 U/L |
| MOPS | 10 mM |
| LiOH | 40 mM |
| EDTA | 20 mM |
| Trehalose | 2% |
| PEG 8000 | 4% |
| BSA | 4% |

EXAMPLE 2

Figure 2:
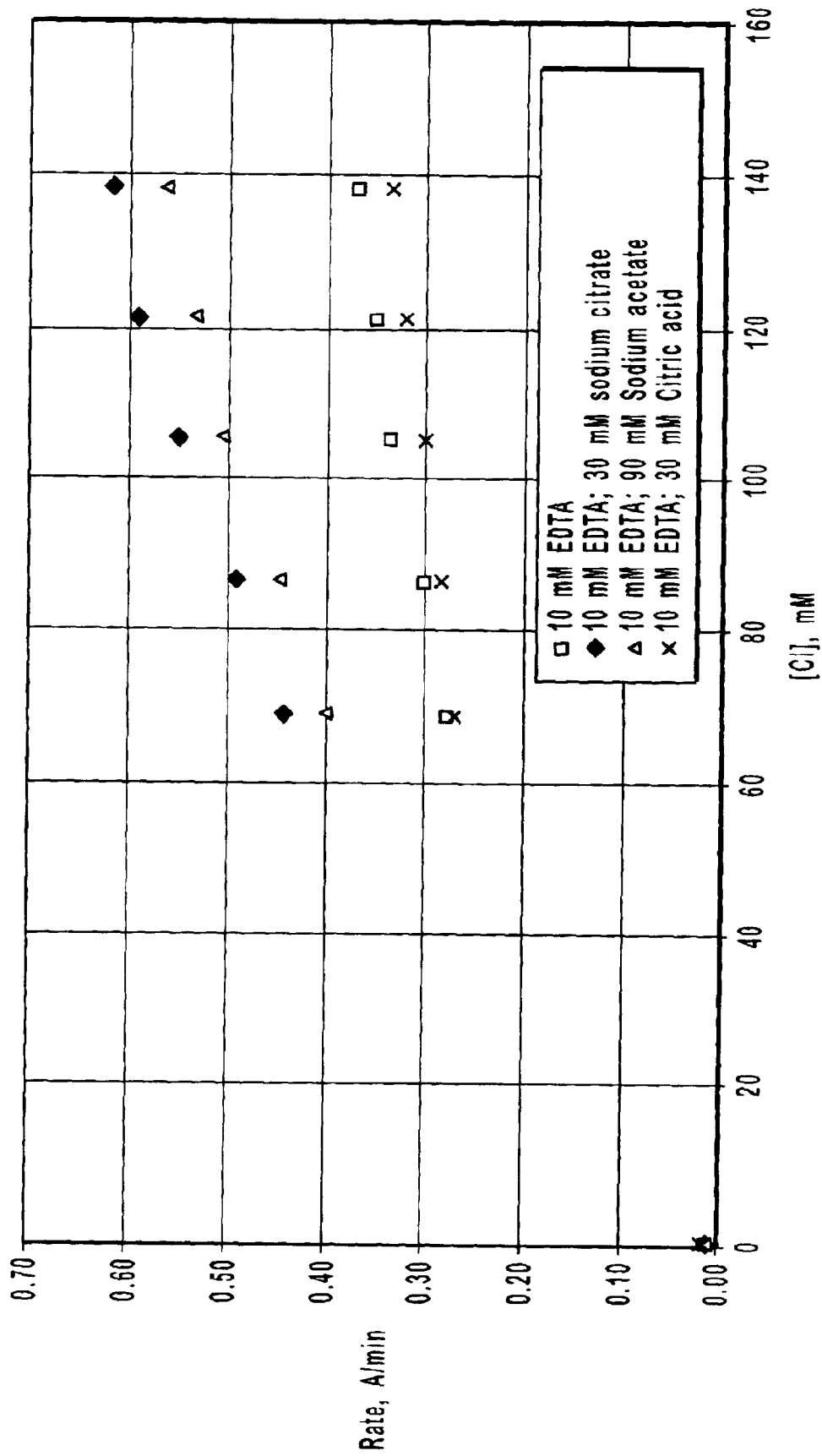
FIG. 2 is a graph showing comparative assays that demonstrate the comparative effects of sodium citrate, sodium acetate, and citric acid on chloride ion determination according to the invention.

A further study was conducted to determine whether the activation of α-amylase was due to the sodium ions or the citrate ions. Four assays were conducted, one with no sodium ions or citrate ions in the enzyme reagent, one with sodium citrate in the enzyme reagent, one with sodium acetate in the enzyme reagent, and one with citric acid in the enzyme reagent. The substrate and enzyme reagents were otherwise prepared as indicated in Tables 1 and 2. Thus, sodium acetate served as the alternate source for sodium and citric acid served as the alternate source for citrate. As illustrated in FIG. 2, the assay with sodium acetate showed a similar activation to the use of sodium acetate while the citric acid assay showed no activation.

EXAMPLE 3

Figure 3:
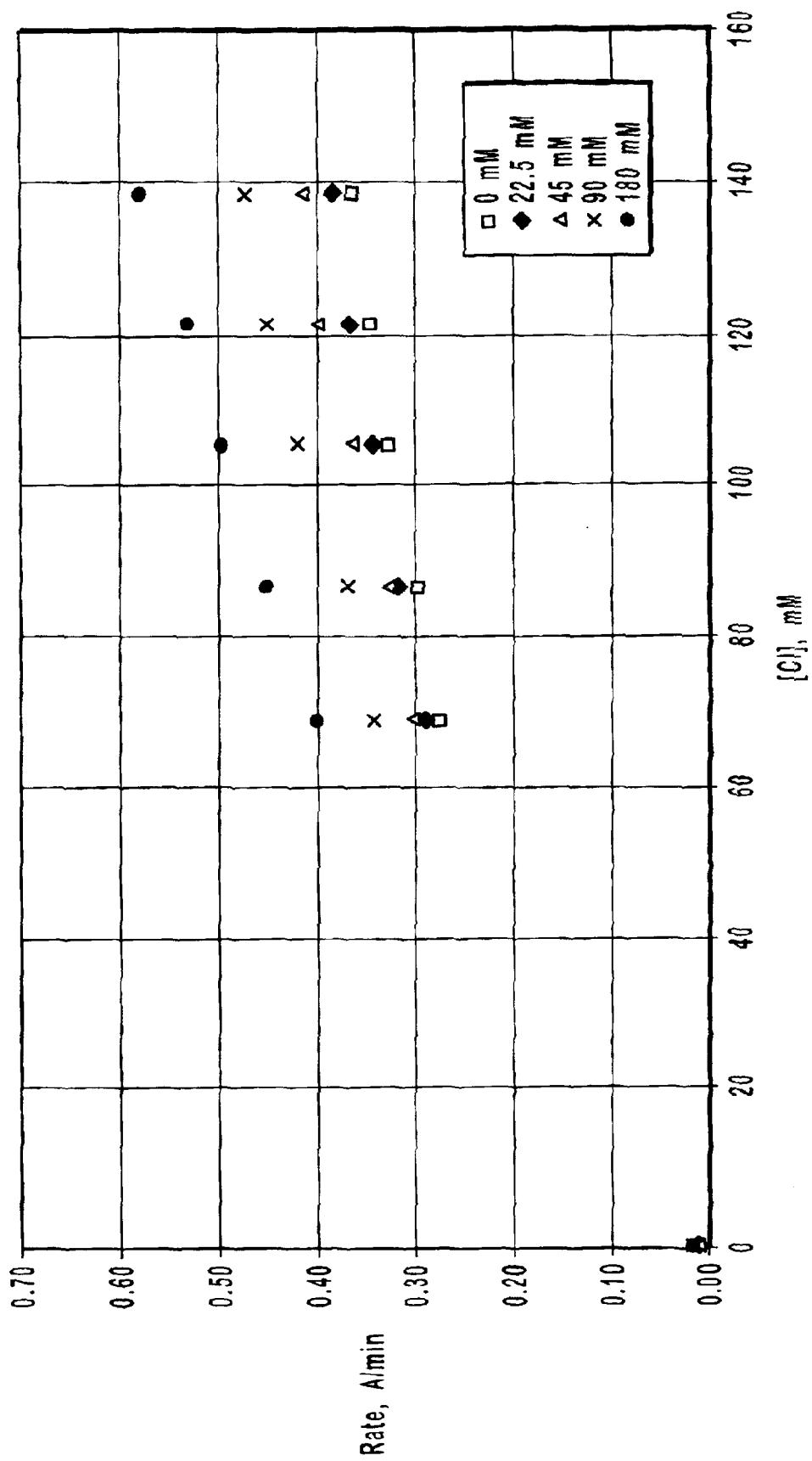
FIG. 3 is a graph showing comparative assays that demonstrate the effect of differing concentrations of sodium citrate on chloride ion determination according to the invention.

Another study was conducted with varying concentrations of sodium acetate. Assays were conducted with sodium acetate concentrations of 0.0 mM, 22.5 mM, 45.0 mM, 90.0 mM, and 180.0 mM. The substrate and enzyme reagents were otherwise prepared as indicated in Tables 1 and 2. Five chloride concentrations were used, varying from approximately 68 mM to approximately 139 mM. As illustrated in FIG. 3, higher concentrations of sodium acetate resulted in increased activation rates.

EXAMPLE 4

Figure 4:
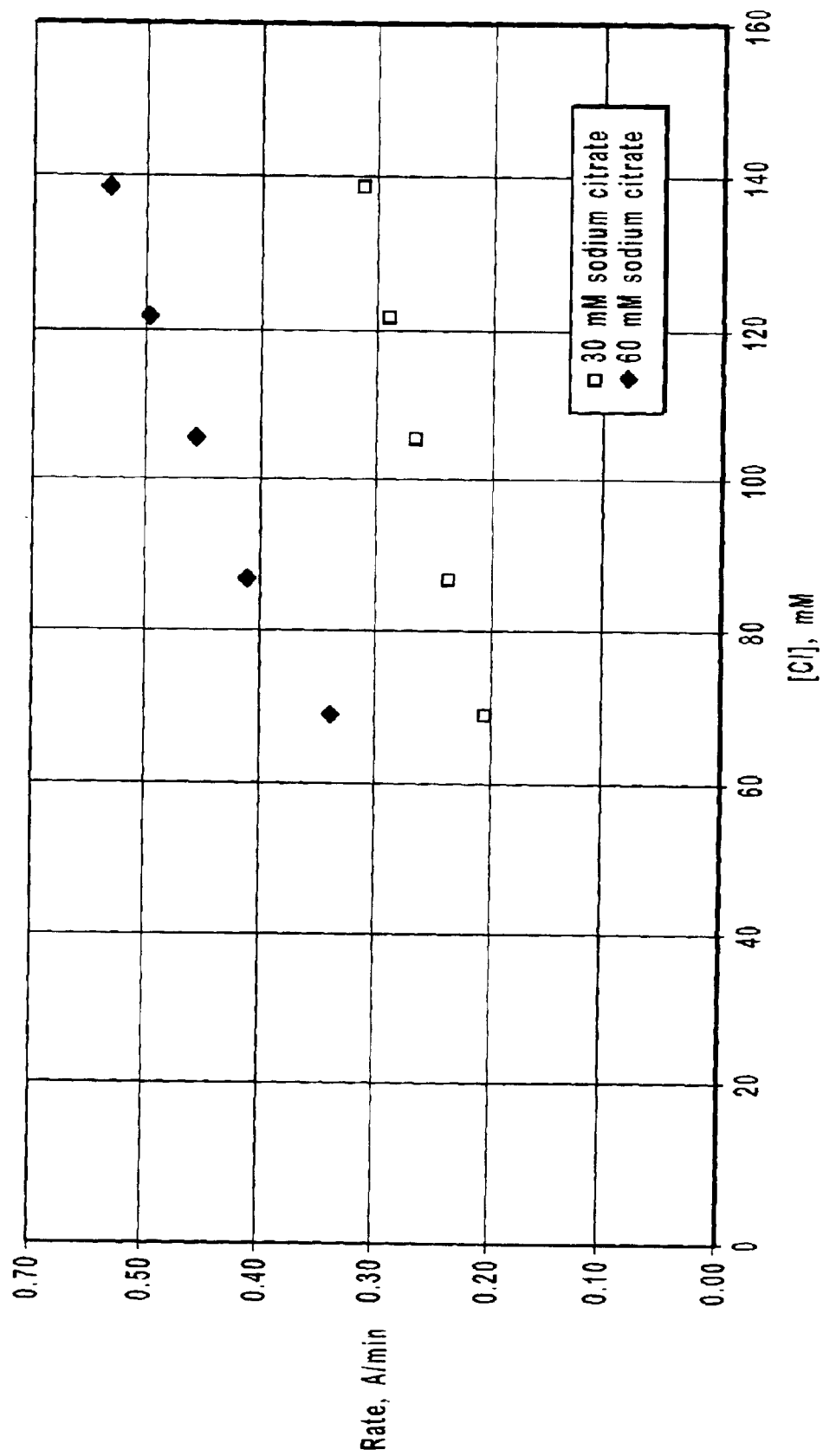
FIG. 4 is a graph showing comparative assays that demonstrate the effect of differing concentrations of sodium citrate in the substrate reagent on chloride ion determination according to the invention.

A sodium-containing substrate reagent and an enzyme reagent were prepared with the following components as listed in Table 3 and Table 4 respectively below. In this study, sodium citrate was added directly to the substrate reagent at concentrations of 30 mM and 60 mM. Five assays were run for each sodium citrate concentration at chloride concentrations of from about 68 to about 139 mM. The study was conducted to compare the substrate reagent with different sodium citrate concentrations. As illustrated in FIG. 4, the samples with higher sodium citrate concentrations showed higher activation rates in each assay.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for determining the concentration of chloride ions in samples, comprising:

combining an enzyme reagent with an α-amylase activity detecting substrate, a sodium ion and a sample containing a chloride ion to be assayed, to form a reaction mixture wherein the enzyme reagent includes α-amylase that is substantially calcium-free, wherein the reaction mixture is substantially free of calcium ions and wherein the concentration of the sodium ion is at a level so that α-amylase is substantially activated by the sodium ion in proportion to the amount of the chloride ion in said sample;

assaying the quantity of α-amylase activated by the sodium ion; and determining the quantity of said chloride ion by reference to said activity of α-amylase.

2. The method according to claim 1, wherein calcium is removed from the α-amylase that is substantially calcium-free by use of a chelating compound.

3. The method according to claim 2, wherein said chelating compound is a member selected from the group consisting of ethylenediaminetetraacetic acid, trans-1,2-cyclohexanediamine-N,N,N',N'-tetraacetic acid, glycol ether diamine tetraacetic acid, iminotetraacetic acid, and diaminopropanetetraacetic acid.

4. The method of claim 2, wherein said chelating compound is ethylenediaminetetraacetic acid.

5. The method according to claim 1, wherein calcium is removed from the α-amylase that is substantially calcium-free by use of a compound that forms a covalent bond with calcium.

6. The method according to claim 1, wherein said α-amylase activity detecting substrate is a member selected from the group consisting of 2-chloro-4-nitrophenyl-α-D-maltotrioside, 4-nitrophenyl-α-D-maltopentaoside and α-glucosidase, 2-chloro-4-nitrophenyl-β-D-maltopentaoside and α-glucosidase and β-glucosidase, 4-nitrophenyl-α-D-maltoheptaoside, α-glucosidase, and 2-chloro-4-nitrophenyl-β-D-maltoheptaoside and α-glucosidase and β-glucosidase.

7. The method according to claim 6, wherein said α-amylase activity detecting substrate is 2-chloro-4-nitrophenyl-α-D-maltotrioside.

8. The method according to claim 1, wherein said sample is a bodily fluid sample.

9. The method according to claim 8, wherein said bodily fluid sample is selected from the group consisting of serum, plasma, and urine.

10. The method of claim 1, wherein said sodium ion is in the form of sodium citrate.

11. The method of claim 1, wherein said sodium ion is in the form of sodium acetate.

12. The method of claim 1, wherein α-amylase is not substantially activated by calcium ion.

13. A composition for use in determining the concentration of a chloride ion in a fluid sample, comprising: α-amylase that is substantially calcium-free, a sodium ion, and an α-amylase activity detecting substrate, wherein the composition is substantially free of chloride ion and substantially free of a calcium ion source capable of releasing calcium ion in the presence of a chloride ion and α-amylase.

14. A composition as in claim 13 further comprising a compound capable of forming a chelate with a calcium ion.

15. A composition according to claim 14, wherein said compound capable of forming a chelate with a calcium ion is a member selected from the group consisting of ethylenediaminetetraacetic acid, trans-1,2-cyclohexanediamine-N,N,N',N'-tetraacetic acid, glycol ether diamine tetraacetic acid, iminotetraacetic acid, and diaminopropanetetraacetic acid.

16. A composition according to claim 14, wherein said compound capable of forming a chelate with a calcium ion is ethylenediaminetetraacetic acid.

17. The composition according to claim 13, wherein said α-amylase activity detecting substrate is a member selected from the group consisting of 2-chloro-4-nitrophenyl-α-D-maltotrioside, 4-nitrophenyl-α-D-maltopentaoside and α-glucosidase, 2-chloro-4-nitrophenyl-β-D-maltopentaoside and α-glucosidase and β-glucosidase, 4-nitrophenyl-α-D-maltoheptaoside, α-glucosidase, and 2-chloro-4-nitrophenyl-β-D-maltoheptaoside and α-glucosidase and β-glucosidase.

18. The composition according to claim 13, wherein said α-amylase activity detecting substrate is 2-chloro-4-nitrophenyl-α-D-maltotrioside.

19. The composition of claim 13, wherein said sodium ion is in the form of sodium citrate.

20. The composition of claim 13, wherein said sodium ion is in the form of sodium acetate.

* * * * *